United States Patent

Takahashi et al.

Patent Number: 5,543,566
Date of Patent: Aug. 6, 1996

[54] PROCESS FOR PREPARING AMINO-POLYCARBOXYLIC ACIDS OR SALTS THEREOF

[75] Inventors: Kiyobumi Takahashi, Tokyo; Teturo Nakahama, Hiroshima-ken, both of Japan

[73] Assignee: Nitto Chemical Industry Co., Ltd., Tokyo, Japan

[21] Appl. No.: 305,293

[22] Filed: Sep. 15, 1994

[30] Foreign Application Priority Data

Sep. 17, 1993 [JP] Japan ................................. 5-253584

[51] Int. Cl.⁶ ................................................ C07C 229/04
[52] U.S. Cl. ........................................................ 562/571
[58] Field of Search ........................................... 562/571

[56] References Cited

U.S. PATENT DOCUMENTS

| | | | |
|---|---|---|---|
| 2,538,024 | 1/1951 | McKinney et al. | 260/465 |
| 2,562,198 | 7/1951 | McKinney et al. | 260/519 |
| 3,637,511 | 1/1972 | Yang | 252/527 |

FOREIGN PATENT DOCUMENTS

| | | | |
|---|---|---|---|
| 0513948 | 11/1992 | European Pat. Off. | C11D 7/32 |
| 4211713 | 10/1993 | Germany | C07C 255/25 |
| 5-70795 | 3/1993 | Japan | C11D 3/33 |

OTHER PUBLICATIONS

J. Am. Chem. Soc., 72, 2599 (1950), Cyanoethylation of Alpha Amino Acids, I. Monocyanoethyl Derivatives, McKinney et al.

J. Am. Chem. Soc., 73, 1641 (1951), Cyanoethylation of Alpha Amino Acids, II. Dicyanoethyl and Tricyanoethyl Derivatives, McKinney et al.

J. Am. Chem. Soc., 74, 1942 (1952), Cyanoethylation of Alpha Amino Acids, III. Hydrolysis of Cyanoethyl Derivatives, McKinney et al.

Chemical Abstracts, vol. 91, 21006a (1979), p. 706.

Chemical Abstracts, vol. 94, 175453t (1981), p. 768.

Chemical Abstracts, vol. 72, 25711g (1970), pp. 340–341.

*Primary Examiner*—Paul F. Shaver
*Assistant Examiner*—Rosalynd A. Williams
*Attorney, Agent, or Firm*—Cushman Darby & Cushman

[57] ABSTRACT

Aspartic acid is reacted with prussic acid and formaldehyde to give an amino-polycarboxylic acid or a salt thereof represented by the following formula:

$$R^1OOC-CH_2-\underset{\underset{R^1OOC}{|}}{CH}-\underset{\underset{R^4}{|}}{N}-R^3 \quad (1)$$

wherein each of $R^1$ and $R^2$ represents a hydrogen atom, an alkali metal or an ammonium group; and each of $R^3$ and $R^4$ represents a hydrogen atom or $-CH_2-COOR^1$, provided that $R^3$ and $R^4$ do not represent a hydrogen atom simultaneously. The amino-polycarboxylic acid which is readily biodegradable and has an excellent chelating ability can be obtained from aspartic acid in a high yield and in a high purity.

13 Claims, No Drawings

PROCESS FOR PREPARING AMINO-POLYCARBOXYLIC ACIDS OR SALTS THEREOF

BACKGROUND OF THE INVENTION

1. Field of the Invention

The present invention relates to a process for preparing an amino-polycarboxylic acid or salts thereof.

2. Description of the Related Art

Amino-polycarboxylic acids possess a chelating ability and thus enable to chelate metals in water. For this property, amino-polycarboxylic acids are employed as chemicals for fibers and dyeing, builders for soap and detergents, complexing agents for metal surface treatment, chemicals for photography, bleaching agents for paper pulp, etc.

Sodium tripolyphosphate conventionally used as builders for detergents has an excellent chelating ability but is known to cause over-nourishment of, rivers, lakes and marshes, when the phosphorus contained therein is released into the environment. For this reason, sodium tripolyphosphate is not employed now.

Zeolite which is currently used as a builder for detergents has a weak chelating ability. Furthermore, zeolite is not biodegradable because of its inorganic nature and thus encounters a problem of environmental pollution. In addition, zeolite is water-insoluble and cannot be used for liquid, especially transparent liquid detergent, which is a restriction from an aspect of application. Furthermore, the water-insoluble nature of zeolite causes problems that zeolite adheres and fix onto the inner wall of a conduit or the like, or deposits at the bottom of rivers to cause sludge.

On the other hand, it is known that amino-polycarboxylic acids have been used as builders for detergents. However, in these known amino-polycarboxylic acids, ethylenediaminetetraacetic acid (EDTA) has an excellent chelating ability but is not biodegradable. Nitrilotriacetic acid (NTA) is somewhat biodegradable but reportedly has a teratogenic effect.

Even other known amino-polycarboxylic acids which have an excellent chelating ability, because of their poor biodegradation property, involve a problem of possible environmental accumulation of heavy metals harmful to the living body, when released to the environment.

A variety of amino-polycarboxylic acids have been investigated but no report has been made on any advantageous process for preparing amino-polycarboxylic acids having an excellent chelating ability and an excellent biodegradation property in an industrial scale.

As processes for preparing amino-polycarboxylic acids which are expected to be biodegradable, there are known a process by reacting an amino acid with a glycidylic acid ester (Japanese Patent Application KOKAI (Laid-Open) No. 63-267750), a process by reacting a sulfonic acid derivative with an amino-polycarboxylic acid (Japanese Patent Application KOKAI No. 5-186416), etc. The amino-polycarboxylic acids prepared by these processes contain a hydroxyl group or a sulfonic acid residue.

As processes for preparing amino-polycarboxylic acids containing a hydroxyl group, there are known a process by reacting a sodium iminodiacetate with glycidylamide (Japanese Patent Application KOKAI No. 2-115152), a process by reacting epoxysuccinic acid with glycine (Japanese Patent Application KOKAI No. 5-70795), etc.

However, these amino-polycarboxylic acids prepared by these processes involve problems that the hydroxyl group is not sufficient for imparting biodegradable property to the acids and the sulfonic acid residue is inferior to a carboxyl group in chelating ability.

SUMMARY OF THE INVENTION

An object of the present invention is to provide a novel process for preparing amino-polycarboxylic acids or salts thereof which is an industrially advantageous process, whereby amino-polycarboxylic acids having an excellent ability of chelating metals and an excellent biodegradable property can be obtained in a high yield in a high purity.

In order to solve the foregoing problems, the present inventors have made extensive investigations and have found that amino-polycarboxylic acids represented by general formula (1) below can be obtained by reacting aspartic acid, prussic acid (hydrocyanic acid) and formaldehyde, and these amino-polycarboxylic acids have an excellent metal chelating ability and are extremely biodegradable. The present invention has thus been accomplished.

It is known that aspartic acid per se has a chelating ability, but its ability is too weak to use aspartic acid as a chelating agent for various applications.

To the contrary, the amino-polycarboxylic acids obtained from aspartic acid in accordance with the process of the present invention are unexpectedly readily biodegradable and also excellent in chelating ability.

The present invention relates to a process for preparing an amino-polycarboxylic acid or salts thereof represented by general formula (1) below, which comprises reacting aspartic acid, prussic acid and formaldehyde:

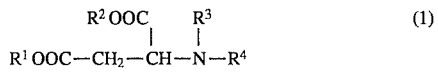

$$R^1OOC-CH_2-CH(R^3)(COOR^2)-N(R^4)\quad(1)$$

wherein each of $R^1$ and $R^2$ represents a hydrogen atom, an alkali metal or an ammonium group; and each of $R^3$ and $R^4$ represents a hydrogen atom or $-CH_2-COOR^1$, provided that $R^3$ and $R^4$ do not represent a hydrogen atom simultaneously.

According to the process of the present invention, amino-polycarboxylic acids which are readily biodegradable and have an excellent chelating ability can be prepared from aspartic acid in a high yield and in a high purity.

DETAILED DESCRIPTION OF THE INVENTION

The amino-polycarboxylic acids represented by general formula (1) above include aspartic acid N-monoacetic acid and aspartic acid N,N-diacetic acid.

The alkali metal salts or ammonium salts shown by general formula (1) include the salts of amino-polycarboxylic acids in which at least one hydrogen atom of 3 to 4 carboxyl groups present in the amino-polycarboxylic acid molecule is substituted with an alkali metal or an ammonium group, and mixed salts thereof.

Examples of the alkali metal include Li, Na, K, Rb, Cs, etc. Thus the alkali metal salts include monolithium salts, dilithium salts, trilithium salts, tetralithium salts; monosodium salts, disodium salts, trisodium salts, tetrasodium salts; monopotassium salts, dipotassium salts, tripotassium salts, tetrapotassium salts; monorubidium salts, dirubidium salts, trirubidium salts, tetrarubidium salts; monocesium salts, dicesium salts, tricesium salts, tetracesium salts; and mixed salts thereof.

Examples of the ammonium group are trimethylammonium, triethylammonium, triisopropylammonium, tributylammonium, tri(hydroxyethyl)ammonium, tetramethylammonium, tetraethylammonium, tetrapropylammonium, tetrabutylammonium, trimethylbenzylammonium, cetyldimethylbenzylammonium, cetylpyridyl, etc. The ammonium salts thus include monoammonium salts, diammonium salts, triammonium salts, tetraammonium salts and mixed salts thereof.

The amino-polycarboxylic acids represented by general formula (1) above have an excellent metal chelating ability and are readily biodegradable. Accordingly, even though these acids are released in the environment, the amino-polycarboxylic acids are readily degraded by microorganisms present in the natural world but do not remain in the environment. Therefore, there is no chance of fixing heavy metals in the environment or accumulating heavy metals in the living body.

Aspartic acid which is used as the starting compound in the process of the present invention is not particularly limited but may be those commercially available. Aspartic acid is an amino acid having asymmetric carbon; in the process of the present invention, any of DL- and L-forms may be employed but L-aspartic acid is preferably used.

The reaction in the process of the present invention is carried out preferably in such a reaction medium that is in a homogeneous solution state. However, the reaction may also be performed in the absence of any solvent.

As the reaction medium used in the process of the present invention, any medium may be used so long as aspartic acid and other starting materials are soluble therein. Water or an organic solvent is typically employed as the medium.

Typical examples of the organic solvent include alcohols such as methanol, ethanol, isopropanol, butanol, etc.; ketones such as acetone, methyl isobutyl ketone, etc.; esters such as methyl acetate, ethyl acetate, butyl acetate, etc.; linear hydrocarbons such as n-pentane, n-hexane, n-heptane, etc.; cyclic hydrocarbons such as cyclohexane, etc.; aromatic hydrocarbons such as benzene, toluene, xylene, etc.; nitriles such as acetonitrile, etc.; ethers such as diethyl ether, dibutyl ether, tetrahydrofuran, dioxane, etc.

These organic solvents may also be used as admixture thereof; in this case, a mixing ratio is optionally chosen.

Preferred examples of the reaction media are water; methanol, ethanol, isopropanol, acetone or acetonitrile; or a mixture of water with at least one of these organic solvents.

These organic solvents may also be mixed with water in an optional proportion.

By reacting aspartic acid, prussic acid and formaldehyde, N-monocyanomethyl- or N,N-dicyanomethyl aspartic acid or a mixture thereof are obtained as intermediates.

In the process of the present invention, prussic acid is employed in a range of 0.2 to 30 moles, preferably 1 to. 15 moles per mole of aspartic acid, and formaldehyde is employed in a range of 0.2 to 30 moles, preferably 1 to 15 moles, per mole of aspartic acid.

By controlling the proportion of prussic acid and formaldehyde to aspartic acid, the proportion of the produced N-monocyanomethyl- and N,N-dicyanomethyl aspartic acid can be controlled.

The reaction of aspartic acid, prussic acid and formaldehyde is carried out preferably under basic conditions using a base. The pH of the reaction system is adjusted in a range of 7 to 13, preferably 7.5 to 11.

Specific examples of the base which may be employed in the above reaction include alkali metal hydroxides or alkaline earth metal hydroxides such as lithium hydroxide, sodium hydroxide, potassium hydroxide, rubidium hydroxide, calcium hydroxide, barium hydroxide, etc.; various alkali metal salts like carbonates, phosphates, borates, aluminates, silicates, etc. of alkali metals, such as sodium carbonate, potassium carbonate, trisodium phosphate, disodium phosphate, sodium pyrophosphate, tripotassium phosphate, dipotassium phosphate, sodium borate, sodium aluminate, sodium silicate, etc.; tertiary amines such as trimethylamine, triethylamine, triisopropylamine, tributylamine, triethanolamine, etc.; quaternary ammonium hydroxide compounds such as tetramethylammonium hydroxide, tetraethylammonium hydroxide, tetrapropylammonium hydroxide, tetrabutylammonium hydroxide, trimethylbenzylammonium hydroxide, cetyldimethylbenzylammonium hydroxide, cetylpyridinium hydroxide, etc.; metal alkoxides such as sodium methoxide, potassium ethoxide, potassium t-butoxide, etc. These bases may be used alone or in combination of two or more in an optional proportion.

Alkali metal hydroxides are preferably employed.

The reaction temperature is in a range of 40 to 180° C., preferably 70 to 140° C.

The reaction time is generally from 30 minutes to 24 hours, preferably 1 to 15 hours.

In the process of the present invention, the cyanomethyl aspartic acid produced by reacting aspartic acid, prussic acid and formaldehyde as described above may be hydrolyzed with an alkali, after or without isolating it from the reaction system. Thus, aspartic acid N-monoacetic acid and/or aspartic acid N,N-diacetic acid can be obtained.

The hydrolysis with an alkali is carried out under basic conditions using a base. The pH of the reaction system is adjusted in a range of 7 to 13, preferably 8 to 12.

The reaction temperature is in a range of 40 to 180° C. preferably 70 to 150° C.

The reaction time is generally from 30 minutes to 24 hours, preferably 1 to 15 hours.

Examples of the base which may be employed for the alkali hydrolysis in the process of the present invention include alkali metal hydroxides such as lithium hydroxide, sodium hydroxide, potassium hydroxide, rubidium hydroxide, etc.; various alkali metal salts like carbonates, phosphates, borates, aluminates, silicates, etc. of alkali metals, such as sodium carbonate, potassium carbonate, trisodium phosphate, disodium phosphate, sodium pyrophosphate, tripotassium phosphate, dipotassium phosphate, sodium borate, sodium aluminate, sodium silicate, etc.; tertiary amines such as trimethylamine, triethylamine, triisopropylamine, tributylamine, triethanolamine, etc.; quaternary ammonium hydroxide compounds such as tetramethylammonium hydroxide, tetraethylammonium hydroxide, tetrapropylammonium hydroxide, tetrabutylammonium hydroxide, trimethylbenzylammonium hydroxide, cetyldimethylbenzylammonium hydroxide, cetylpyridinium hydroxide, etc.; metal alkoxides such as sodium methoxide, potassium ethoxide, potassium t-butoxide, etc.

These bases may be chosen depending upon kind of cations in the amino-polycarboxylic acid salts which are the desired final products. The bases may be used alone or in combination of two or more in an optional proportion.

Alkali metal hydroxides and quaternary ammonium hydroxides are preferably employed.

In the reaction solution after the alkali hydrolysis was completed, aspartic acid N-monoacetic acid and/or aspartic acid N,N-diacetic acid are dissolved in the form of alkali metal salts, ammonium salts or the like, depending on kind of bases used for the alkali hydrolysis. These salts may be isolated as crystals from the reaction mixture through crystallization by cooling or concentration.

Further by adding an acid to the reaction mixture after the alkali hydrolysis or to the aforesaid salts isolated by crystallization from the reaction mixture, aspartic acid N-monoacetic acid and/or aspartic acid N,N-diacetic acid can be obtained as the free acid(s).

As the acid used for the above acid treatment, there are mineral acids such as hydrochloric acid, sulfuric acid, nitric acid, phosphoric acid, etc., and organic acids such as acetic acid, oxalic acid, etc.

Aspartic acid N-monoacetic acid and/or aspartic acid N,N-diacetic acid formed as the free acid(s) by the acid treatment described above can be isolated as crystals from the reaction mixture after the acid treatment, through crystallization by cooling or concentration.

Aspartic acid N-monoacetic acid and/or aspartic acid N,N-diacetic acid separated from the reaction mixture may be purified, if necessary, by recrystallization using a solvent.

As the solvent for recrystallization, water or an organic solvent may be used. As the organic solvent, there may be used any of a water-miscible solvent such as methanol, ethanol, isopropanol, acetone, acetonitrile, etc., and a water-immiscible solvent such as n-hexane, ethyl acetate, ethyl ether, toluene, etc. These organic solvents may be used alone or as admixture thereof. It is preferred to use water, methanol, ethanol, isopropanol, acetone or acetonitrile, or a mixture of water with these organic solvents.

Aspartic acid N-monoacetic acid and/or aspartic acid N,N-diacetic acid thus obtained may be converted, if necessary, into the corresponding alkali metal salts or ammonium salts in a conventional manner, for example, using a base containing, e.g., an alkali metal or an ammonium group.

Hereunder the present invention is described more specifically by referring to the examples but should not be construed to be limited thereto.

EXAMPLE 1

In a reaction vessel were charged 133.1 g of L-aspartic acid, 175.0 g of 48% aqueous sodium hydroxide solution and 90.0 g of water. The temperature was elevated to 90° C. A mixture of 28.4 g of prussic acid, 85.2 g of 37% aqueous formaldehyde solution and 94.2 g of 48% aqueous sodium hydroxide solution was dropwise added to the above mixture at 105° C. over 3 hours. After the completion of the dropwise addition, the reaction mixture was stirred at 105° C. for further 2 hours.

Then 15 g of 48% aqueous sodium hydroxide solution was added to the reaction mixture containing N-monocyanomethyl aspartic acid. The resulting mixture was stirred at 110° C. for 3 hours for the alkali hydrolysis.

After the alkali hydrolysis was completed, 15 g of 10% aqueous formaldehyde solution was added to the system to decompose the remaining prussic acid. Then 245.2 g of 40% aqueous sulfuric acid solution was added to the mixture and the resulting precipitated crystals were filtered to give 180.2 g of L-aspartic acid N-monoacetic acid as crude crystals.

The crude crystals were recrystallized from a solvent mixture of water and methanol to give 175.0 g (yield: 91.6%) of purified L-aspartic acid N-monoacetic acid.

Analysis of the thus obtained purified L-aspartic acid N-monoacetic acid by high performance liquid chromatography showed a purity of 100%.

EXAMPLES 2 to 6

Various aspartic acids were reacted with prussic acid and formaldehyde in a manner similar to Example 1, under the reaction conditions shown in Table 1. The cyanomethyl aspartic acids thus obtained were subjected to the alkali hydrolysis and precipitated with an acid to give aspartic acid N-monoacetic acid or aspartic acid N,N-diacetic acid in the DL- or L-form. The results are shown in Table 1.

TABLE 1

| No. | Cyanomethylation | | | | | | | |
|---|---|---|---|---|---|---|---|---|
| | Amount Charged (g) | | | Solution Added Dropwise (g) | | | Temperature (°C.) | Time (hr) |
| | Aspartic acid | 48% NaOH | Water | HCN | 37% HCHO | 48% NaOH | | |
| Example 1 | L-form | 133.1 | 175.0 | 90.0 | 28.4 | 85.2 | 94.2 | 105 | 5 |
| Example 2 | DL-form | 133.1 | 175.0 | 90.0 | 28.4 | 85.2 | 94.2 | 90 | 8 |
| Example 3 | DL-form | 133.1 | 175.0 | 90.0 | 28.4 | 85.2 | 94.2 | 120 | 4 |
| Example 4 | DL-form | 133.1 | 175.0 | 90.0 | 62.5 | 187.4 | 212.0 | 90 | 12 |
| Example 5 | L-form | 133.1 | 175.0 | 90.0 | 62.5 | 187.4 | 212.0 | 105 | 8 |
| Example 6 | DL-form | 133.1 | 175.0 | 180.0 | 62.5 | 187.4 | 212.0 | 120 | 6 |

| No. | Alkali Hydrolysis | | | Acid precipitation | Product | | |
|---|---|---|---|---|---|---|---|
| | 48% NaOH (g) | Temperature (°C.) | Time (hr) | 40% sulfuric acid (g) | Kind | Yield amount (g) | Yield (%) |
| Example 1 | 15.0 | 110 | 3 | 245.2 | L-Aspartic acid N-monoacetic acid | 175.0 | 91.6 |
| Example 2 | 15.0 | 110 | 3 | 245.2 | DL-Aspartic acid N-monoacetic acid | 168.5 | 88.2 |
| Example 3 | 15.0 | 140 | 1 | 245.2 | DL-Aspartic acid N-monoacetic acid | 167.8 | 87.8 |
| Example 4 | 25.0 | 120 | 2 | 564.0 | DL-Aspartic acid N,N-diacetic acid | 190.5 | 76.5 |
| Example 5 | 25.0 | 120 | 2 | 564.0 | L-Aspartic acid N,N-diacetic acid | 201.7 | 80.9 |
| Example 6 | 25.0 | 140 | 1 | 564.0 | DL-Aspartic acid N,N-diacetic acid | 198.5 | 79.7 |

What is claimed is:

1. A process for preparing an amino-polycarboxylic acid or a salt thereof represented by general formula (1):

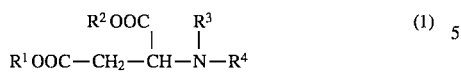

wherein each of $R^1$ and $R^2$ represents a hydrogen atom, an alkali metal or an ammonium group; and each of $R^3$ and $R^4$ represents a hydrogen atom or $-CH_2-COOR^1$, provided that $R^3$ and $R^4$ do not represent a hydrogen atom simultaneously, which comprises the steps of reacting aspartic acid, prussic acid and formaldehyde, subjecting cyanomethyl aspartic acids produced as intermediates, to a hydrolysis with an alkali to form an amino-polycarboxylic acid salt corresponding to the alkali, and optionally treating the amino-polycarboxylic acid salt with an acid to form the corresponding amino-polycarboxylic acid.

2. A process for preparing an amino-poly-carboxylic acid or a salt thereof according to claim 1, wherein said aminopolycarboxylic acid is aspartic acid N-monoacetic acid, aspartic acid N,N-diacetic acid or both.

3. A process for preparing an amino-polycarboxylic acid or a salt thereof according to claim 1, wherein said salt is an alkali metal salt or an ammonium salt.

4. A process for preparing an amino-polycarboxylic acid or a salt thereof according to claim 1, wherein said aspartic acid is L-aspartic acid.

5. A process for preparing an amino-polycarboxylic acid or a salt thereof according to claim 1, wherein prussic acid is employed in a range of 0.2 to 30 moles and formaldehyde is employed in a range of 0.2 to 30 moles, per mole of aspartic acid.

6. A process for preparing an amino-polycarboxylic acid or a salt thereof according to claim 1, wherein prussic acid is employed in a range of 1 to 15 moles and formaldehyde is employed in a range of 1 to 15 moles, per mole of aspartic acid.

7. A process for preparing an amino-polycarboxylic acid or a salt thereof according to claim 1, wherein aspartic acid is reacted with prussic acid and formaldehyde at a pH in a range of 7 to 13.

8. A process for preparing an amino-polycarboxylic acid or a salt thereof according to claim 1, wherein aspartic acid is reacted with prussic acid and formaldehyde at a pH in a range of 7.5 to 11.

9. A process for preparing an amino-polycarboxylic acid or a salt thereof according to claim 1, wherein the cyanomethyl aspartic acids formed by reacting aspartic acid with prussic acid and formaldehyde is subjected to a hydrolysis with an alkali without isolating the intermediates.

10. A process for preparing an amino-polycarboxylic acid or a salt thereof according to claim 1, wherein said hydrolysis is carried out at a pH in a range of 8 to 12.

11. A process for preparing an amino-polycarboxylic acid or a salt thereof according to claim 1, wherein a reaction mixture after the hydrolysis or the salt isolated from the reaction solution is treated with an acid.

12. A process for preparing an amino-polycarboxylic acid or a salt thereof according to claim 11, wherein said acid is at least one selected from the group consisting of hydrochloroic acid, sulfuric acid, nitric acid, phosphoric acid, acetic acid and oxalic acid.

13. A process for preparing an aminopolycarboxylic acid or a salt thereof according to claim 1, wherein said cyanomethyl aspartic acid produced as intermediates by reacting aspartic acid with prussic acid and formaldehyde is subjected to a hydrolysis with an alkali after isolating said intermediates.

* * * * *